United States Patent [19]
Shaw

[11] Patent Number: 5,535,635
[45] Date of Patent: Jul. 16, 1996

[54] COMPOSITE SAMPLE STORAGE AND MEASUREMENT SYSTEM

[75] Inventor: Daniel G. Shaw, Conroe, Tex.

[73] Assignee: McFarland Pump Co., Houston, Tex.

[21] Appl. No.: 367,373

[22] Filed: Dec. 30, 1994

[51] Int. Cl.[6] ........................................... G01N 1/10
[52] U.S. Cl. ................... 73/863.84; 73/864.62; 177/2; 177/50
[58] Field of Search ................ 177/1, 50, 2; 73/863.02, 73/863.84, 864.61, 864.62, 863, 863.01; 436/29; 422/63, 68.1, 81, 82, 102, 103; 210/85, 86

[56] References Cited

U.S. PATENT DOCUMENTS

| | | | |
|---|---|---|---|
| 2,418,876 | 4/1947 | Grace, Jr. . | |
| 2,592,464 | 4/1952 | Plank | 73/864.62 |
| 2,636,387 | 4/1953 | McKinney et al. | 73/864.62 |
| 2,637,211 | 5/1953 | Norman | 73/864.62 |
| 2,794,344 | 6/1957 | Boren | 73/863.84 |
| 3,160,016 | 12/1964 | Middleton | 73/864.62 |
| 3,253,469 | 5/1966 | Norman | 73/864.62 |
| 3,504,549 | 4/1970 | Davis et al. . | |
| 3,593,533 | 7/1971 | Washington . | |
| 3,681,997 | 8/1972 | Allen et al. . | |
| 4,532,813 | 8/1985 | Rinehart | 73/863.84 |
| 5,092,988 | 3/1992 | Womack, II et al. | 210/85 |

OTHER PUBLICATIONS

McFarland Pump Co. brochure dated Oct., 1993, bottom section of page.

*Primary Examiner*—Joseph W. Drodge

[57] ABSTRACT

Composite sample storage and measurement system having a divided vessel for receiving samples, the first part of which stores the samples received, and a second part of which, isolated by a flexible membrane, contains a standard fluid which is displaced to a reservoir to determine the weight of standard fluid displaced, and therefore, the volume of sample received. The reservoir, the flexible line from vessel to reservoir and the vessel are maintained under superatmospheric pressure to assure sample integrity.

6 Claims, 1 Drawing Sheet

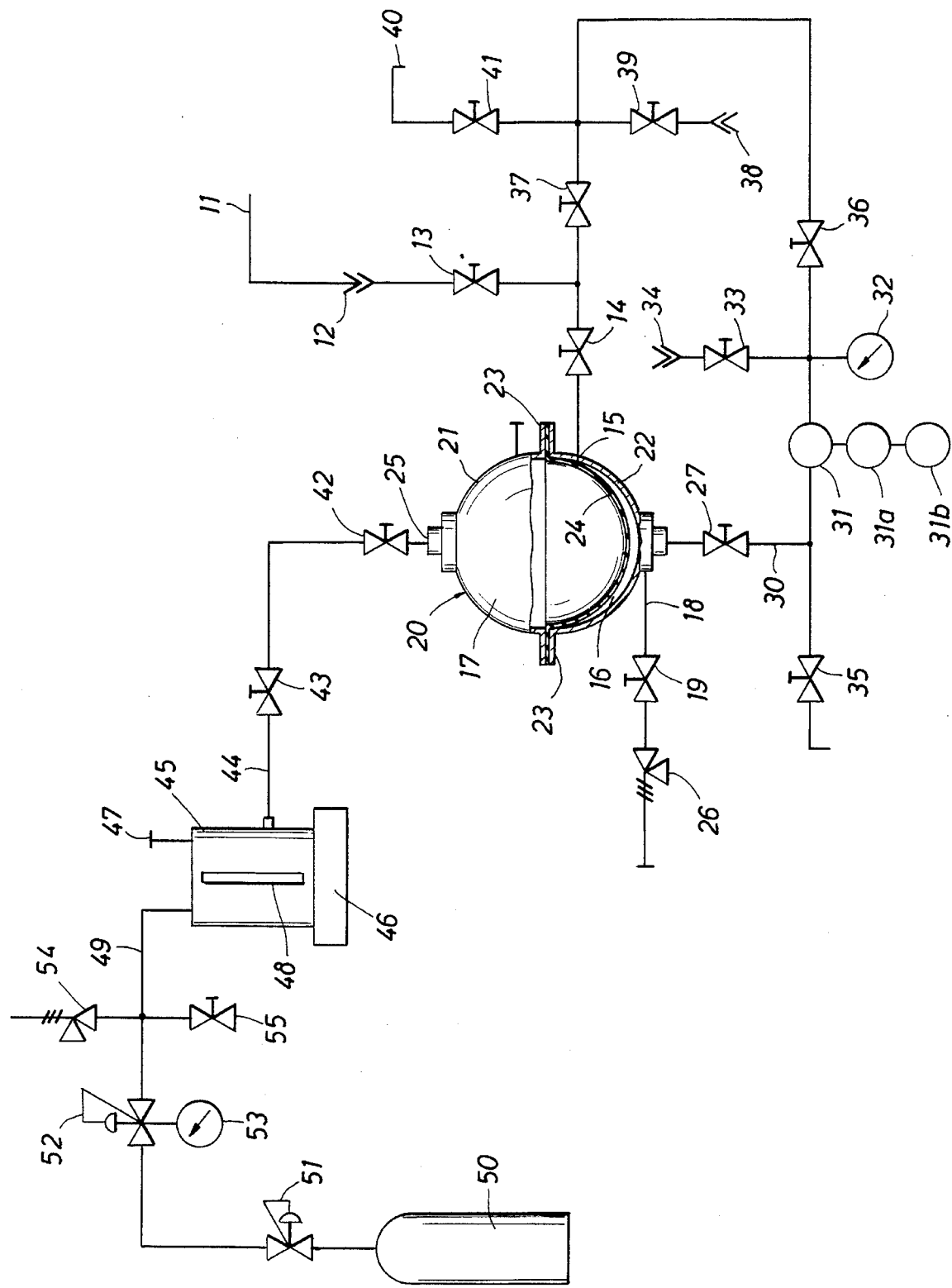

COMPOSITE SAMPLE STORAGE AND MEASUREMENT SYSTEM

FIELD OF THE INVENTION

This invention relates to sampling storage and measurement for samples of flow streams.

BACKGROUND OF THE INVENTION

Samplers for extracting equal volume samples from flowing streams are well known in the art. For example, a sampling connection may be made in a pipeline to extract several samples over time to represent the "average" contents of the stream over a given period. Those samples flow into a storage container from which representative samples may be taken for analytical tests of the materials. The results of the analytical tests are taken as the representation of the contents which have flowed past the test point in the pipeline over a given time.

Some samplers take samples more or less frequently or larger or smaller samples, both proportional to pipeline flow rates. Other systems simply take timed or periodic samples of the same size. Whatever the frequency or size of samples taken, a record of the size of the sample is necessary. Equally important is the maintenance of sample integrity in the case of the presence of volatile constituents in the sample. Another important aspect is the representative accuracy of the composite sample to be analyzed, given that varying individual sample numbers and sizes of individual samples may be taken in the period in question.

SUMMARY OF THE INVENTION

The invention includes a vessel into which a sample is received, means for isolating the sample from a standard fluid in a second part of the vessel which displaces from the vessel an amount of standard fluid equal to the sample received in the vessel, means to transfer the standard fluid to a reservoir, means to weigh the reservoir and standard fluid therein, and a pressure source to impose a super-atmospheric pressure on the vessel, the reservoir and the transferring means when in fluid connection with each other.

Certain embodiments of the invention include means to extract, recirculate and homogenize the cumulated samples in the vessel.

The invention solves the problem of accurate individual sample size determination and preserves the integrity of the composite stored sample.

BRIEF DESCRIPTION OF THE DRAWING

The drawing shows a generally schematic view of the sample measuring and storage system, with the sample vessel shown in partial cross-section.

DESCRIPTION OF THE PREFERRED EMBODIMENT

Reference is now made to the drawing in which a preferred embodiment of the sample storage and measurement system is shown. The sampling line 11 leads from a pipeline (not shown), through a sampling device (not shown) to a pipeline disconnect 12. Sampling devices for extracting a sample from the stream flowing in the pipeline are well known and may be of the fixed volume or variable volume type. Such samplers may operate responsive to pipeline flow rate or by timer to take differing sample sizes or more or less frequent samples.

Downstream of pipeline disconnect 12 are the ball valves 13 and 14 leading to a spherical sample vessel generally designated by numeral 20. Sample vessel 20 is comprised of the hemispherical upper part 21 and the hemispherical lower part 22. Parts 21, 22 are joined at their intersection by the vessel flanges 23. Between flanges 23, which are held together by bolts or the like (not shown) a flexible diaphragm 24 is sealed therebetween at its periphery. Diaphragm 24 is sufficiently flexible that its central portion may be moved from a position close to lower part 22 (in the absence of samples in vessel 20) to a position close to upper part 21 when vessel 20 is essentially full of sample.

Vessel 20 contains a sample inlet 15 for admitting the sample from sampling line 11 into the sample space 16, bounded by lower part 22 and diaphragm 24. Prior to entry of a sample into sample space 16, diaphragm 24 is at its lowermost position, having negligible volume in sample space 16. Prior to any samples being received, the volume of vessel 20 (less the volume of diaphragm 24) is filled by a standard fluid such as glycol in standard fluid space 17. Vessel 20 is of rigid construction and in operation, is always filled by noncompressible sample and standard fluid. Therefore, as a sample is received in sample space 16, the precisely corresponding volume of standard fluid will be displaced from vessel 20 at the standard fluid outlet 25. Diaphragm 24 isolates the sample from contamination by the standard fluid and assists, together with the pressure imposed on the system, to maintain composite sample integrity. Diaphragm 24 insures that there will be no dissolution or transfer of sample constituents into the standard fluid.

Also in fluid communication with sample space 16 is a vessel pressure relief line 18, a vessel ball valve 19 and a vessel pressure relief valve 26. In the event excessive pressure from the pipeline should find its way to vessel 20, vessel ball valve 19 would be opened and vessel pressure relief valve 26 would relieve such pressure prior to damaging vessel 20 and other components of the system.

Also in fluid communication with sample space 16 and sample inlet 15 is a recirculation line 30. Recirculation line 30 is for the purpose of circulating the sample in sample space 16 from vessel 20, through the pump 31 and back into sample inlet 15 in order to recirculate and homogenize the sample prior to analysis. Recirculation line 30 also includes a recirculation ball valve 27, a sample pressure indicator 32, a sample ball valve 33 and the quick disconnect 34 by which samples may be delivered for analysis. Recirculation line 30 also includes the recirculation drain valve 35 for purging or draining recirculation line 30. Pump 31 is powered by a motor 31b through the speed reducer gearing 31a.

To complete the sample recirculating circuit, recirculation ball valves 36, 37 can isolate a second sample connection 38, its associated ball valve 39 and a high point vent 40 and its associated ball valve 41. High point vent 40 and ball valve 41 permit the filling of the sample recirculating circuit prior to operation of the system.

Standard fluid outlet 25 is connected through shutoff valves 42 and 43 to a flexible reservoir line 44 leading to a standard fluid reservoir 45. Standard fluid reservoir 45 rests on a balance 46 or other weighing mechanism. If necessary, standard fluid may be put into standard fluid reservoir 45 through the fill line 47. Fill line 47 is normally closed during operation of the system. Standard fluid reservoir 45 is also equipped with a site glass 48 to determine in a rough fashion the approximate contents of standard fluid reservoir 45.

In fluid communication with an upper portion of standard fluid reservoir 45 is a flexible pressure line 49 which leads to a pressure source 50 containing a pressurized gas such as nitrogen. Pressure line 49 carries the pressurized gas from pressure source 50 and imposes a predetermined pressure on the fluid in standard fluid reservoir 45, pressure line 44 and vessel 20 when those parts of the system are in fluid communication with each other. Interposed in pressure line 49 are a high pressure limit valve 51, a low pressure limit valve 52 and its associated pressure gauge 53 and a gas pressure relief valve 54. Gas pressure relief valve 54 also includes a gas drain ball valve 55.

It is to be noted that reservoir line 44 and pressure line 49 are flexible lines that will not induce error in the weighing of standard fluid reservoir 45. As will be described below, the accuracy of the use of balance 46 is an important feature of the invention.

In operation, a sample of a given size is injected into sampling line 11 with ball valves 13, 14, 19, 27, 36 and 37 in the open position. The sample is received in vessel 20 through sample inlet 15 and into sample space 16. Shutoff valves 42 and 43 are in the open position. The sample admission into sample space 16 causes diaphragm 24 to move, thus displacing a quantity of standard fluid from standard fluid space 17 in a volume exactly equal to the sample admitted into vessel 20.

The amount of standard fluid displaced from standard fluid space 17 flows through reservoir line 44 and into the tared standard fluid reservoir 45. Reservoir and the standard fluid therein 45 is weighed, and by knowing the density of the standard fluid, the volume of sample taken can be determined. Care should be taken that the pressure imposed on the system by low pressure limit valve 52 be the same before and after the admission of each individual sample. Balance 46 may be connected to a graph or digital recorder (not shown) to record the time and size of each sample and of the cumulated sample during the sampling period. Such recorders are well known in the art.

When it is desired to obtain an analysis of the cumulated sample, it is desirable, in order to obtain accurate analysis, to recirculate and make homogeneous the sample in sample space 16. Pump 31 is actuated and the cumulated sample is pumped through recirculation line 30 and returned to sample space 16 a sufficient number of times to assure sample homogeneity. A sample for analysis may then be taken at quick disconnect 34 or sample connection 38.

The pressure on the system during sample taking and storage imposed by pressure source 50 may be selected according to the anticipated contents of the composite sample to be obtained. Pressures such as 50 p.s.i.g. at the high pressure limit valve 51 and 15 p.s.i.g. at the lower pressure limit valve 52 have been found to be acceptable for crude oil samples. Samples with greater volatile constituents such as propane or other dissolved petroleum gases may require higher pressures imposed on the system to retain sample integrity.

Thus, a unique composite sample storage and measurement system has been described herein. Parts may be rearranged and equivalent structures which retain the attributes of the system may be substituted in an embodiment without departing from the inventive concept.

What is claimed is:

1. A pressurized cumulative sampling and measuring system including:

a cumulative fluid containing sample collecting vessel;

an inlet in said vessel for receiving a series of samples in a first part thereof;

means for isolating said samples from a standard fluid so as to incrementally displace respective volumes of standard fluid from a second part of said vessel equal to the volume of each of said samples received into said vessel;

means for transferring the volume of standard fluid displaced by said isolating means to a reservoir;

means for weighing said reservoir and said displaced volume of standard fluid; and means for imposing a constant predetermined superatmospheric pressure on each of said vessel, said transferring means and said reservoir when they are in fluid connection with each other to maintain said samples' integrity, said vessel, said transferring means and said weighing means all being fluidly connectable.

2. The system as claimed in claim 1, further including:

means to recirculate and homogenize the cumulative fluid samples.

3. The system as claimed in claim 1, wherein:

said vessel is spherical and comprised of two hemispherical parts; and said isolating means is a diaphragm sealed at the intersection of such hemispherical parts and of sufficient flexibility to displace substantially all said standard fluid or said samples from said vessel.

4. The system as claimed in claim 1, including:

means for automatically recording the weight of said reservoir and said displaced volume of standard fluid following each time a volume of standard fluid is transferred to said reservoir.

5. A pressurized cumulative sampling and measuring system including:

a vessel of fixed volume having two separated fluid compartments;

flexible means separating said compartments for ejecting a volume of fluid from a first of said compartments responsive to the admission of fluid to a second of said compartments and equal to the volume of fluid admitted to said second compartment;

means for transferring the ejected volume of fluid to a reservoir;

means for weighing only said reservoir and its contents;

said reservoir, said transferring means and said vessel all being fluidly connectable; and, means for imposing a constant predetermined pressure on said reservoir when in fluid connection with said transferring means and said vessel to maintain integrity of said fluid in said second compartment.

6. The system as claimed in claim 5, wherein:

said vessel is spherical having two hemispherical sections;

one of said sections has an inlet for admitting a volume of fluid;

the other of said sections has an outlet for ejecting a volume of fluid; and, said flexible means takes the form of a fluid impermeable hemispherical bladder sealed to each of said hemispherical sections at their intersection.

\* \* \* \* \*